United States Patent
Yang et al.

(10) Patent No.: US 7,470,535 B2
(45) Date of Patent: Dec. 30, 2008

(54) STATIC DIFFUSION CELL FOR DIFFUSION SAMPLING SYSTEMS

(75) Inventors: Hua Yang, Foster City, CA (US); Delphine Caroline Imbert, Cupertino, CA (US)

(73) Assignee: ALZA Corporation, Mountain View, CA (US)

( * ) Notice: Subject to any disclaimer, the term of this patent is extended or adjusted under 35 U.S.C. 154(b) by 620 days.

(21) Appl. No.: 10/810,453

(22) Filed: Mar. 27, 2004

(65) Prior Publication Data

US 2005/0019903 A1    Jan. 27, 2005

Related U.S. Application Data

(60) Provisional application No. 60/458,905, filed on Mar. 28, 2003.

(51) Int. Cl.
    *C12M 1/12*     (2006.01)
    *C12M 1/34*     (2006.01)
    *G01N 13/04*     (2006.01)
    *B01L 11/00*     (2006.01)
    *B01D 63/08*     (2006.01)

(52) U.S. Cl. ............. 435/297.1; 435/297.2; 435/297.4; 422/101; 422/102; 73/64.47; 210/321.75; 210/321.84

(58) Field of Classification Search ............. 435/297.1, 435/297.2, 297.5; 73/64.47; 210/321.75, 210/321.84
See application file for complete search history.

(56) References Cited

U.S. PATENT DOCUMENTS

| | | | | |
|---|---|---|---|---|
| 4,667,504 A | * | 5/1987 | Hobson ......................... | 73/38 |
| 5,972,694 A | * | 10/1999 | Mathus ...................... | 435/288.4 |
| 6,521,191 B1 | * | 2/2003 | Schenk et al. ............... | 422/102 |

OTHER PUBLICATIONS

International Search Report for Corresponding Application No. PCT/US2004/009193, Aug. 2004.
Bosman, I.J. et al. "Novel diffusion cell for in vitro transdermal permeation, compatible with automated dynamic sampling", Journal of Pharmaceutical and Biomedical Analysis 14 (1996); pp. 1015-1023.
Chattaraj, S.C. et al. "A simple diffusion cell to monitor drug release from semi-solid dosage forms", International Journal of Pharmaceutics 120 (1995); pp. 119-124.

* cited by examiner

*Primary Examiner*—William H Beisner
(74) *Attorney, Agent, or Firm*—Diehl Servilla LLC; Scott S. Servilla; Karen M. Whitney

(57) ABSTRACT

A new design for a static diffusion cell for use in a diffusion sampling apparatus to be used in conjunction with automated or manual sampling is disclosed. The diffusion cell of present invention provides to an improved and efficient diffusion assay system.

10 Claims, 11 Drawing Sheets

Prior Art

Prior Art

US 7,470,535 B2

STATIC DIFFUSION CELL FOR DIFFUSION SAMPLING SYSTEMS

CROSS-REFERENCE TO RELATED APPLICATION

Pursuant to the provisions of 35 U.S.C. § 119(e), this application claims the benefit of the filing date of provisional patent application Ser. No. 60/458,905, filed Mar. 28, 2003, for "Static Diffusion Cell for Diffusion Sampling Systems."

BACKGROUND OF THE INVENTION

1. Field of the Invention

The present invention relates to static diffusion cells useful in automated and manual diffusion sampling systems as well as assay methods that utilize diffusion sampling systems that include one or more diffusion cells according to the present invention. In particular, the present invention provides a static diffusion cell that includes a single chambered receptor compartment, which design reduces or eliminates the disadvantages associated with diffusion cells having multi-chambered receptor compartments and allows for improved sampling systems and assay methods.

2. Description of the Related Art

In vitro membrane diffusion systems with automated sampling are widely available for flow-through diffusion cells. However, applicants are presently aware of only two commercial systems that provide both static diffusion cells and automated sampling. Hanson Research Corp. of Chatsworth, Calif., sells the Hanson Microetteplus™ Transdermal Diffusion System, and Logan Instruments Corp. of Somerset, N.J., sells the Logan System-902 and Logan System-912 Automated Transdermal Sampling Systems. Logan also plans to sell an upgraded system that includes a cell design similar to the 902-system and an XYZ robot for automatic sampling. Although, the diffusion systems available from Hanson Research and Logan Instruments exhibit differences in design, the systems available from both companies includes a large amount of small diameter tubing and pumps (peristaltic or syringe) that move fluids through multiple compartments within the systems.

As illustrated in FIG. 1, in the Logan system 10, tubing is part of the cell design. The receptor compartment consists of three chambers linked together by small diameter tubing. A diffusion membrane 11 is positioned on the diffusion chamber 12, which includes a stir bar 14, a sampling port 16 that allows introduction of a sampling probe 18, and a water jacket 20 with an inlet and an outlet that facilitate circulation of water around the diffusion chamber 12 to maintain the diffusion chamber 12 at a desired temperature, such as 37° C. A material or formulation to be evaluated 22 is placed over the diffusion membrane 11, and samples are collected from the collection chamber or flow cell 28 using a suitable collection apparatus. The third chamber 24 is used as a bubble trap. A peristaltic pump 26 continuously circulates the receptor medium 30 between the three chambers to maintain adequate mixing, except at sampling time. After receptor medium 30 flows out of the diffusion chamber 12 and flows through both the collection chamber 28 and the bubble trap 24, the receptor medium 30 returns to the diffusion chamber 12 through a media return 32. Process steps for the Logan system 10 include 1) taking a sample from the flow cell 28; 2) collecting the sample in an HPLC sample rack 34, wherein on-line injection is optional; 3) using gravity flow 40 from a replacement media bottle 38 to feed replacement media into a replacement media cell 36 obtained from the HPLC sample rack 34; and 4) adding the replacement media 36 at the flow cell 28 after sampling.

As illustrated in FIG. 2, in the Hanson MicroettePlus™ Transdermal Diffusion System 50, the diffusion cell 54 consists of a single chamber, but the input arm of the receptor chamber is connected by tubing to a syringe chamber 52 (Microette unit) and the output arm to a central sample collection chamber 56. Samples from the receptor chambers are collected in the central sample collection chamber 56 by positive displacement initiated by the syringe unit 52. Therefore, the Microetteplus™ Transdermal Diffusion System 50 also utilizes multiple chambers interconnected by tubing.

The designs of the systems described above can make cell set-up, handling, and cleaning difficult and can lead to inaccurate experimental data. In particular, the relatively extensive use of tubing in the systems available from Logan Instruments Corp. and Hanson Research Corp. introduces several potential problems. For example, the tubing can clog or leak, and the use of tubing can result in variable or inaccurate calculations of cell volume. Perhaps even more problematic is binding of media constituents, such as the material to be assayed, to the tubing or leaching of chemicals from the tubing into the receptor medium. Both the binding of materials from the receptor medium to the tubing and the leaching of materials from the tubing into the receptor medium can lead to an inaccurate assay of the amount or type of materials that diffuse through the diffusion membrane and into the receptor medium.

Further, systems designed according to those available from Logan Instruments Corp. and Hanson Research Corp. permit the accumulation of air bubbles under the diffusion membrane even after receptor medium has been degassed. Accumulation of air bubbles under the diffusion membrane causes a reduction in the area of the diffusion membrane in contact with the receptor medium, thereby reducing the effective diffusion area. Such a reduction in diffusion area can, in turn, result in inaccurate experimental data. However, removing air bubbles from the systems available from Logan Instruments Corp. and Hanson Research Corp. system is tedious at set-up and very difficult or even unattainable once a diffusion experiment has started. Accordingly, when these systems are used, they typically require supervision to ensure that air bubbles do not accumulate under the diffusion membrane, which supervision defeats, at least in part, the purpose of having an automated sampling process.

SUMMARY OF THE INVENTION

In one aspect, the present invention is directed to a new design for a diffusion cell that can be used in conjunction with automated or manual sampling systems. In particular, the present invention provides a diffusion cell that integrates a diffusion chamber, sampling chamber, and bubble trap into a single receptor compartment. The cell design of the present invention allows for a diffusion cell that is completely free of tubing.

In another aspect, the present invention includes a diffusion sampling system that incorporates one or more diffusion cells according to the present invention.

In yet another aspect, the present invention an assay method that utilizes a diffusion sampling system according to the present invention.

DETAILED DESCRIPTION OF THE INVENTION

Figure 1:
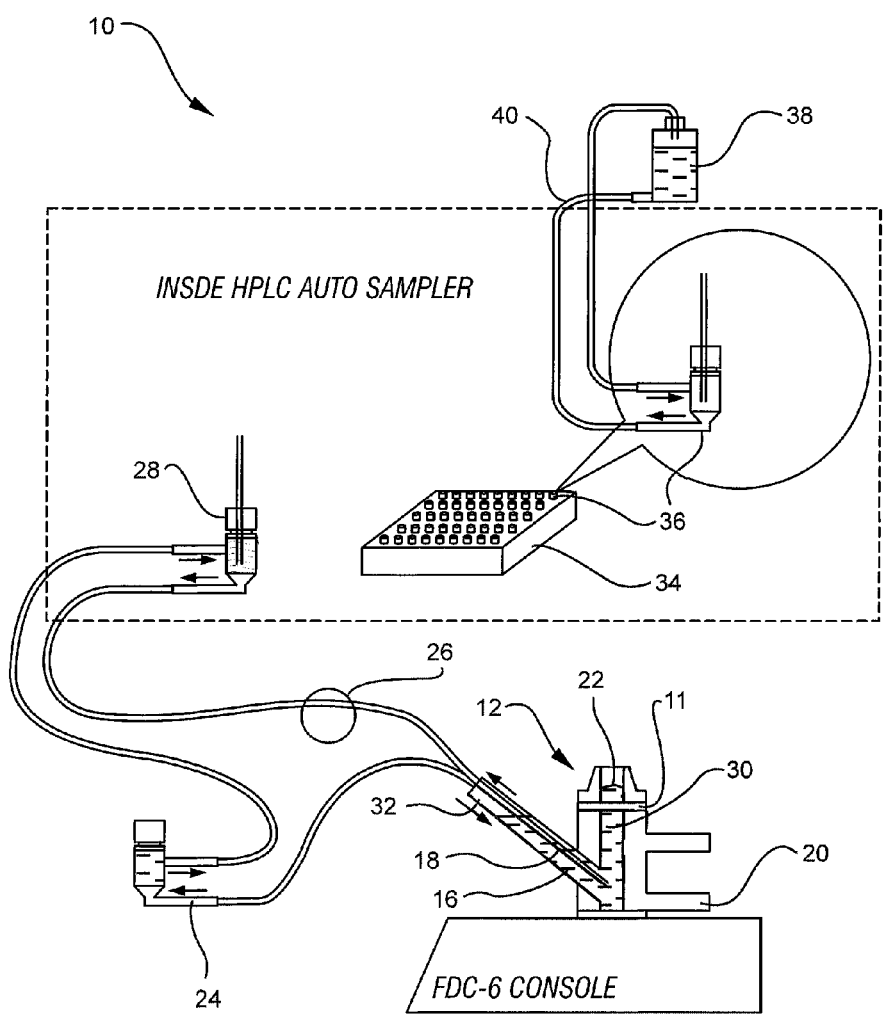
FIG. 1 provides a schematic illustration of a Logan System-902 Transdermal Sampling System showing the three-chamber diffusion cell.
Figure 2:
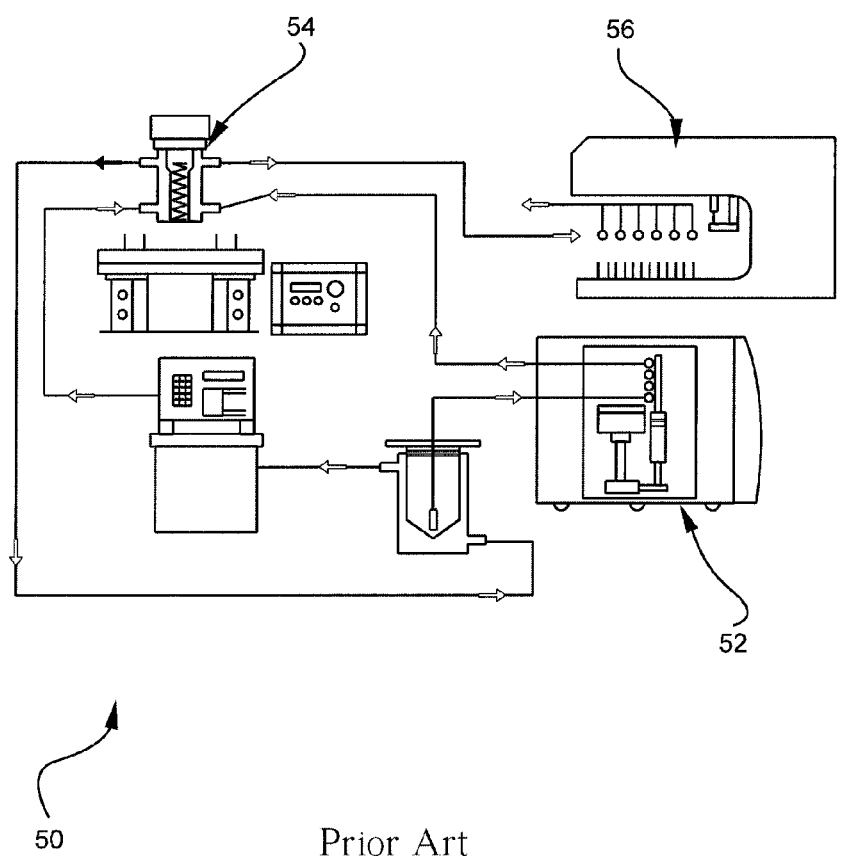
FIG. 2 provides a schematic illustration of the Hanson MicroettePlus™ Transdermal Diffusion System.

In one aspect, the present invention is directed to a new design for a diffusion cell that can be used in conjunction with automated or manual sampling systems. In particular, the present invention provides a diffusion cell that integrates a diffusion chamber, sampling chamber, and bubble trap into a single receptor compartment. The cell design of the present invention allows for a diffusion cell that is completely free of tubing. Moreover, the design of a diffusion cell according to the present invention eliminates the need for a pump for circulating the fluid within various chambers.

It is believed that the design of the diffusion cell of the present invention has several advantages over diffusion cell designs that include multiple compartments, wherein the receptor medium flows into the different compartments through tubing that places the compartments in fluid communication. For example, relative to systems requiring the interconnection of multiple compartments via lengths of tubing, the diffusion cells of the present invention can be easily removed and replaced within a diffusion apparatus, which eases experimental set-up and cleaning. Moreover, in diffusion systems including multiple chambers interconnected by tubing, calculation of the cell volume includes assessment of the receptor fluid within the tubing, which makes an accurate determination of cell volume difficult. In contrast, because diffusion cells of the present invention include a single-chambered receptor compartment, diffusion cells of the present invention allow easier and more accurate determination of cell volume. The absence of tubing in a diffusion cell according to the present invention also eliminates potential tube leaks and clogs as well as the problems that result from binding of receptor medium materials to tube walls or leaching of chemicals from the tubing into the receptor medium. Diffusion cells designed according to the present invention are also ease the tasks of replenishing receptor medium and maintaining the receptor medium at a constant volume within the diffusion cell.

Further, unlike existing sampling systems (e.g., the Hanson and the Logan systems described earlier), the diffusion cell design of the present invention allows for relatively easy removal of bubbles appearing under the surface of the diffusion membrane during the course of the experiment. In preferred embodiments, the static diffusion cell of the present invention is designed to automatically reduce the possibility of accumulation of air bubbles at the surface of the diffusion membrane exposed to the receptor compartment.

Each embodiment of the diffusion cell of the present invention illustrated herein is shown without a water jacket. Existing diffusion cells are often designed to include a water jacket, which serves to control the temperature of the diffusion cell by circulating water of a desired temperature around at least a portion of the receptor compartment. Though the diffusion cell of the present invention can be designed to include a water jacket, if desired, presently preferred embodiments do not include such a feature. Eliminating the water jacket further simplifies the design of the diffusion cell, and, in particular, eliminates the need for the tubing and fixtures to support such a temperature regulating system. In addition, control of the temperature within the diffusion cells of the present invention can be achieved through alternative means. For example, temperature control of a diffusion cell according to the present invention can be achieved by positioning the diffusion cell within a mounting block that is regulated to a desired temperature and is designed to accommodate one or more diffusion cells.

Figure 3:
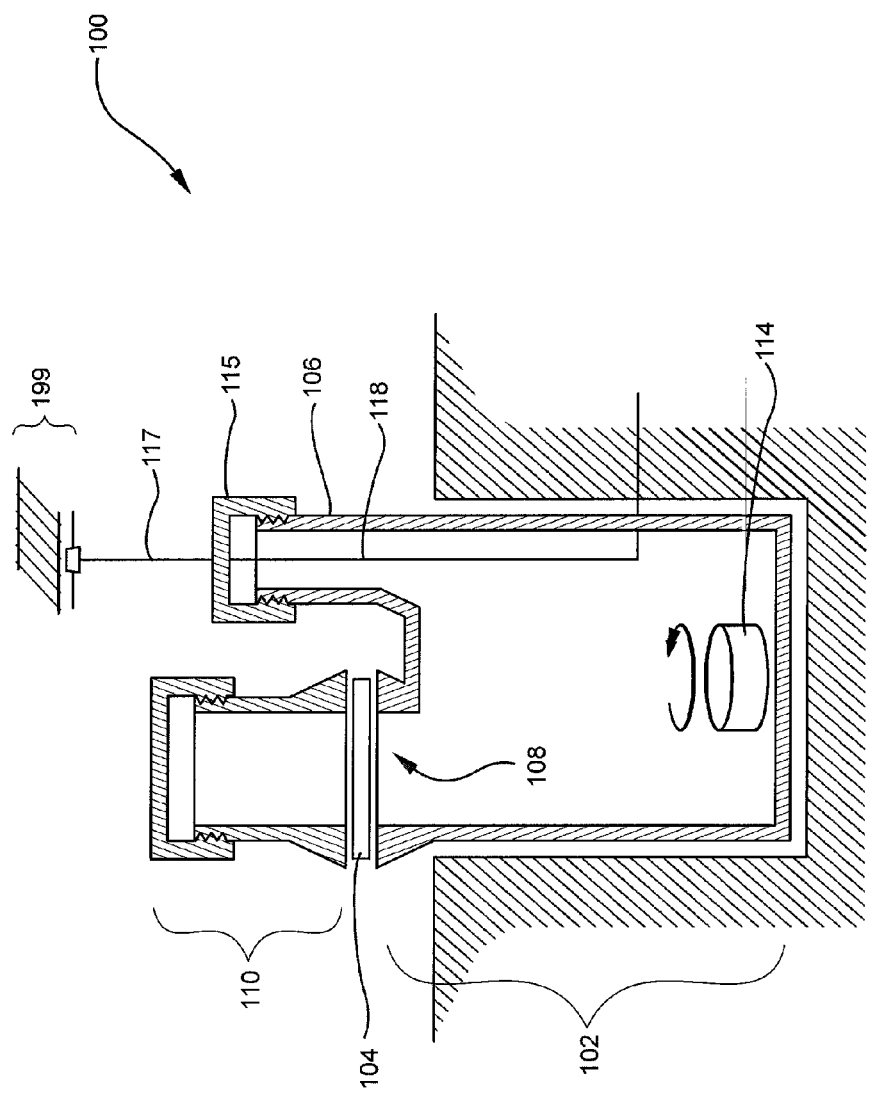
FIG. 3 provides a schematic illustration of a diffusion cell according to the present invention, wherein the sampling arm and bubble trap are part of the receptor compartment.

A first embodiment of the diffusion cell 100 of the present invention is illustrated in FIG. 3. The diffusion cell 100 of the present invention includes a single-chamber receptor compartment 102, a donor compartment 110, a diffusion membrane 104, and a sampling arm 106. As can be seen in FIG. 3, the diffusion membrane 104 is positioned over a first outlet 108 and once the diffusion cell 100 is assembled, a top surface of the diffusion membrane 104 forms at least a portion of the bottom surface of the donor compartment 110, and a bottom surface of the diffusion membrane 104 forms at least a portion of the top surface of the receptor compartment 102. The diffusion membrane 104 used in a diffusion cell 100 according to the present invention may be any natural or synthetic material suitable for application in a diffusion cell. Natural membranes useful in a diffusion cell 100 according to the present invention include, but are not limited to, skin, mucosal membranes, cornea, and epithelial membranes (e.g., intestinal, colonic, or nasal epithelial membranes). In a preferred embodiment, the diffusion membrane 104 is formed of animal or human skin.

Figure 13:
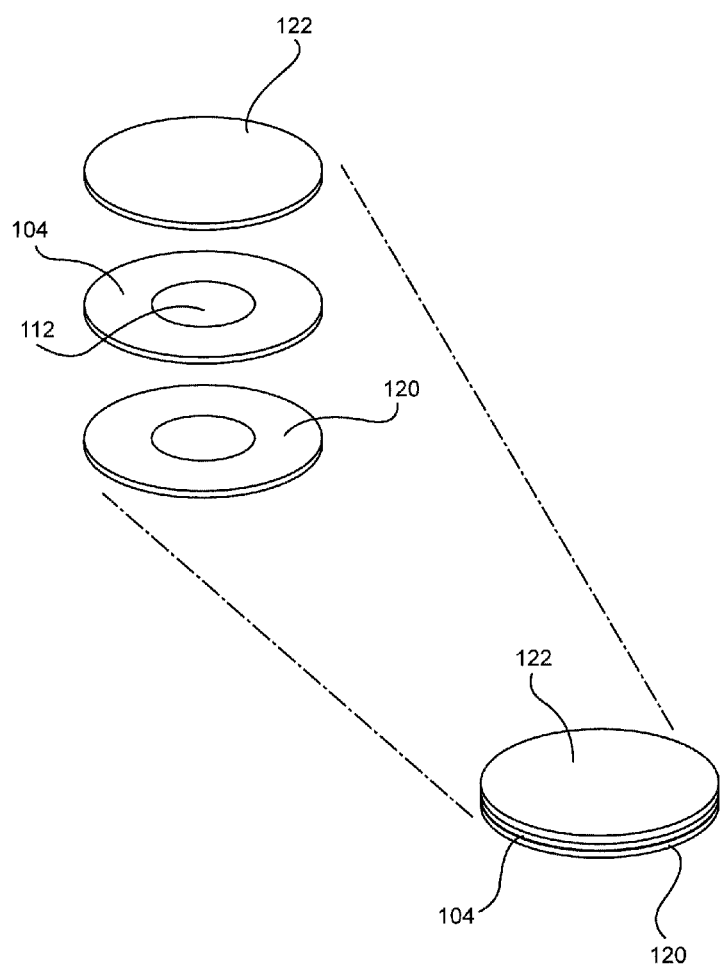
FIG. 13 illustrates a reinforcing ring for use with a diffusion membrane in a diffusion cell of the present invention.

In order to ensure the diffusion membrane is properly held in place between the donor 110 and receptor 102 compartments, the diffusion membrane 104 may be positioned over or disposed between a device or component that reinforces the diffusion membrane 104 and allows the diffusion membrane 104 to be securely held in place without undesired damage to the membrane 104. As is illustrated in FIG. 13, in preferred embodiments, a reinforcing ring 120, such as a washer or gasket, is positioned under the diffusion membrane 104 or over the diffusion membrane 104. Alternatively, two reinforcing rings 120 may be positioned both over and under the diffusion membrane 104. A reinforcing ring 120 used in a diffusion cell 100 of the present invention can be formed of any suitable material, such as a polymer material. In addition, a cover material 122, such as a cover fabric (shown in FIG. 13), can be positioned over the diffusion membrane 104 and test material 112.

A test material 112 is deposited in the donor compartment 110 in contact with the top surface of the diffusion membrane 104. The test material 112 includes one or more constituents, such as one or more drugs, to be tested for permeability or flux across the diffusion membrane 104. Though in preferred embodiments the diffusion cell 100 of the present invention is used to evaluate the flux of one or more drugs contained in a test material 112 across the diffusion membrane 104, diffusion cells 100 according to the present invention are not so limited in use. A diffusion cell 100 according to the present invention can be used to evaluate the permeability or flux of virtually any desired substance across a chosen diffusion membrane 104. The test material 112, therefore, can include a wide range of substances or formulations. For example, the test material 112 may simply be a desired amount of a particular compound at a chosen purity. Alternatively, the test material 112 may include a formulation of two or more materials, such as a liquid formulation (e.g., a solution, suspension, emulsion, etc.) or a lotion, cream, gel, or other semisolid formulation. Even further, the test material 112 may include a drug delivery device, such as a transdermal therapeutic device, designed to delivery a chosen substance, such as one or more therapeutic agents.

The receptor compartment 102 of a diffusion cell 100 of the present invention may be designed according to any desired size or shape. However, the geometry of the receptor compartment 102 is preferably designed for efficient stirring of the receptor medium. The receptor compartment 102 typically includes a magnetic stir bar 114 or other suitable means to ensure proper stirring of the receptor medium throughout the diffusion cell 100, which reduces the possibility of forming stagnant diffusion layers near the diffusion membrane 104. A receptor compartment 102 of a diffusion cell 100 according to the present invention also includes the first outlet 108 and a second outlet 118.

The first outlet 108 may be formed to any size and shape that allows positioning of the diffusion membrane 104 over the first opening 108. For example, where the receptor compartment 102 is designed to accommodate a 5-30 ml volume of receptor medium, the first opening 108 is preferably sized from about 0.7 to about 5 cm$^2$. However, the size and shape of the first opening 108 can be varied, as desired, to allow the use of differently sized diffusion membranes 104 and to suit any particular test conditions. As can be seen in FIG. 3, the first opening 108 can also be adapted to facilitate positioning of the diffusion membrane 104 and association of the donor compartment 110 with the receptor compartment 102. The first outlet 108 and donor compartment 110 of the diffusion cell 100 illustrated in FIG. 3, are designed with a flange that facilitate clamping of the donor compartment 110 over the diffusion membrane 104 and the first opening 108 of the receptor compartment 102. Of course, it is to be understood that the donor compartment 110 can be associated with the receptor compartment 102 using any suitable mechanism, not just a clamp. For example, the donor compartment 110 can be associated with the receptor compartment 102 using a threaded connection, a male-female connection, a snap-fit connection, or through a friction or interference fit. Both the donor compartment 110 and the receptor compartment 102, including the first opening 108, can be adapted as necessary to facilitate the use of a desired mechanism for the association of the donor compartment 110 with the receptor compartment 102.

The second outlet 118 of the receptor compartment 102 serves as a sampling arm 106 and a bubble trap. The second outlet 118 may be sized and shaped according to any desired configuration providing a suitable sampling arm 106. Typically, the opening of the second outlet 118 will be smaller than that of first outlet 108. The second outlet 118 includes a cap or a seal 115 having a septum that can be penetrated by a sampling needle 117. Typically the opening of the second outlet 118 will be circular in shape and will be about 0.5 cm in diameter. In preferred embodiments, the second outlet 118 is sized and shaped so that HPLC vial caps 115 with a septum can be used to cap the second outlet 118.

The sampling arm 106 formed at the second outlet 118 also serves as a bubble trap, allowing the removal of bubbles that form under the diffusion membrane 104. Depending on the design of the diffusion cell 100 of the present invention, bubbles are removed either by tilting the cell 100 and forcing the bubbles from under the diffusion membrane 104 and into the sampling arm 106, or the diffusion cell 100 may be designed such that bubbles forming within the cell 100 automatically migrate into the sampling arm 106 formed by the second outlet 118. If large bubbles accumulate in the sampling arm 106 and the total receptor medium level decreases, more receptor medium can be easily added through the sampling arm 106 to keep the total receptor medium level constant.

The donor compartment 110 of a diffusion cell 100 according to the present invention is positioned over the first opening 108 of the receptor compartment 102 and can be sized and shaped as desired to meet any experimental need. The donor compartment 110 is designed to contain the test material 112. A cap or seal 105, such as a screw cap, septum, or the like, may be provided over the donor compartment 110 and may be necessary where the test material 112 is a liquid or low viscosity or where evaporation or contamination of the test material 112 are to be reduced or eliminated. As is indicated above, the donor compartment 110 can be associated with the receptor compartment 102 using any suitable mechanism. For example, the donor compartment 110 may be clamped to the receptor compartment 102 or, alternatively, the donor compartment 110 may be associated with the receptor compartment 102 using a threaded connection, a male-female connection, a snap-fit connection or by a friction or interference fit. Therefore, the design of one or more components forming the donor compartment 110 can be adapted to facilitate association of the donor compartment 110 with the receptor compartment 102 according to any desired mechanism. In each embodiment, the mechanism for associating the donor compartment 110 with the receptor compartment 102 maintains the donor compartment 110 in close contacting relationship with the diffusion membrane 104 or the first opening 108 of the receptor compartment 102. Though the means for associating the donor compartment 110 with the receptor compartment 102 may form an adequate seal between the two compartments 102, 110 and the diffusion membrane 104, one or more additional sealing elements, such as one or more O-rings or gaskets, may be used where the diffusion membrane 104, donor compartment 110, or receptor compartment 102 interface with one or more other components of the diffusion cell 100.

Figure 4:
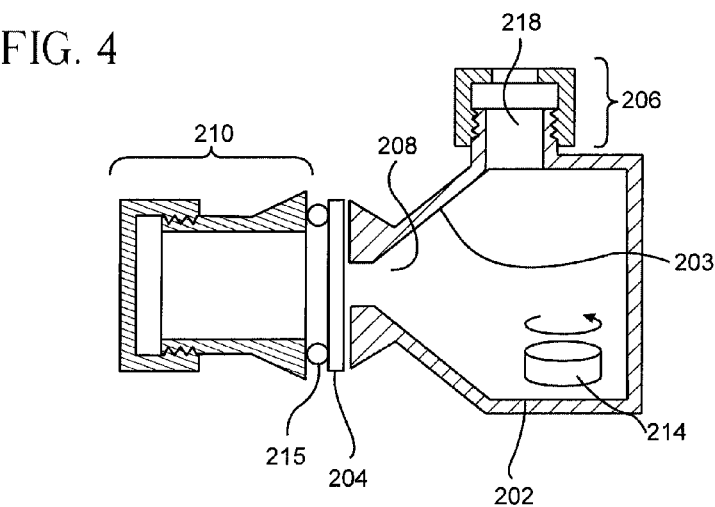
FIG. 4 provides a schematic illustration of a diffusion cell according to the present invention, wherein the first opening of the receptor compartment is positioned on the side of the cell, preventing accumulation of air bubbles under the diffusion membrane.
Figure 5:
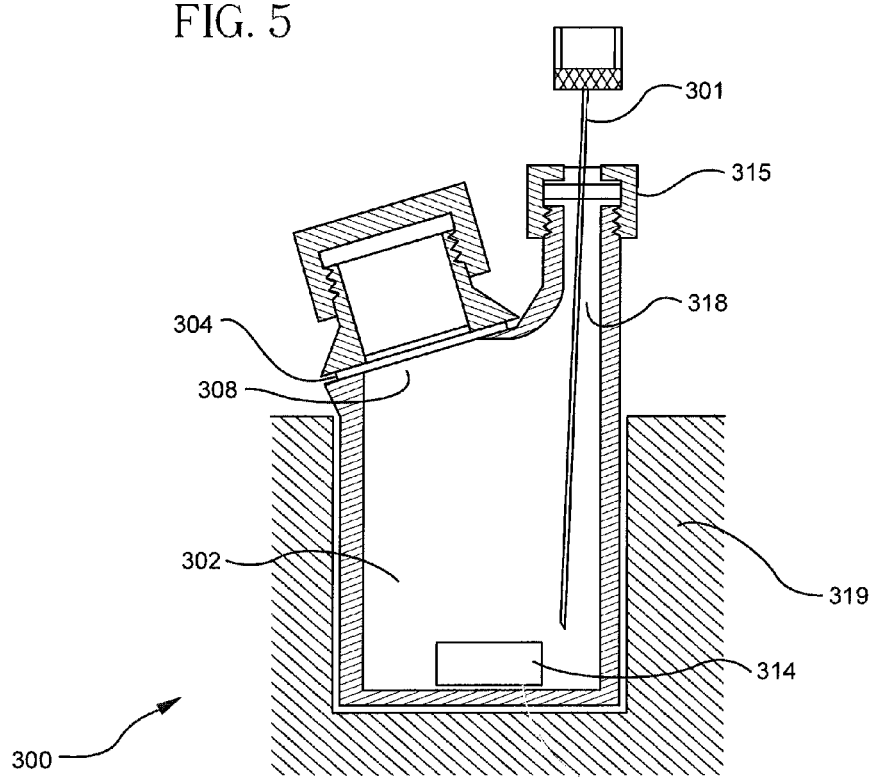
FIG. 5 provides a schematic illustration of a diffusion cell according to the present invention, wherein the first opening creates a diffusion area that is tilted upward toward the second opening, which works to prevent accumulation of air bubbles under the diffusion membrane.
Figure 8:
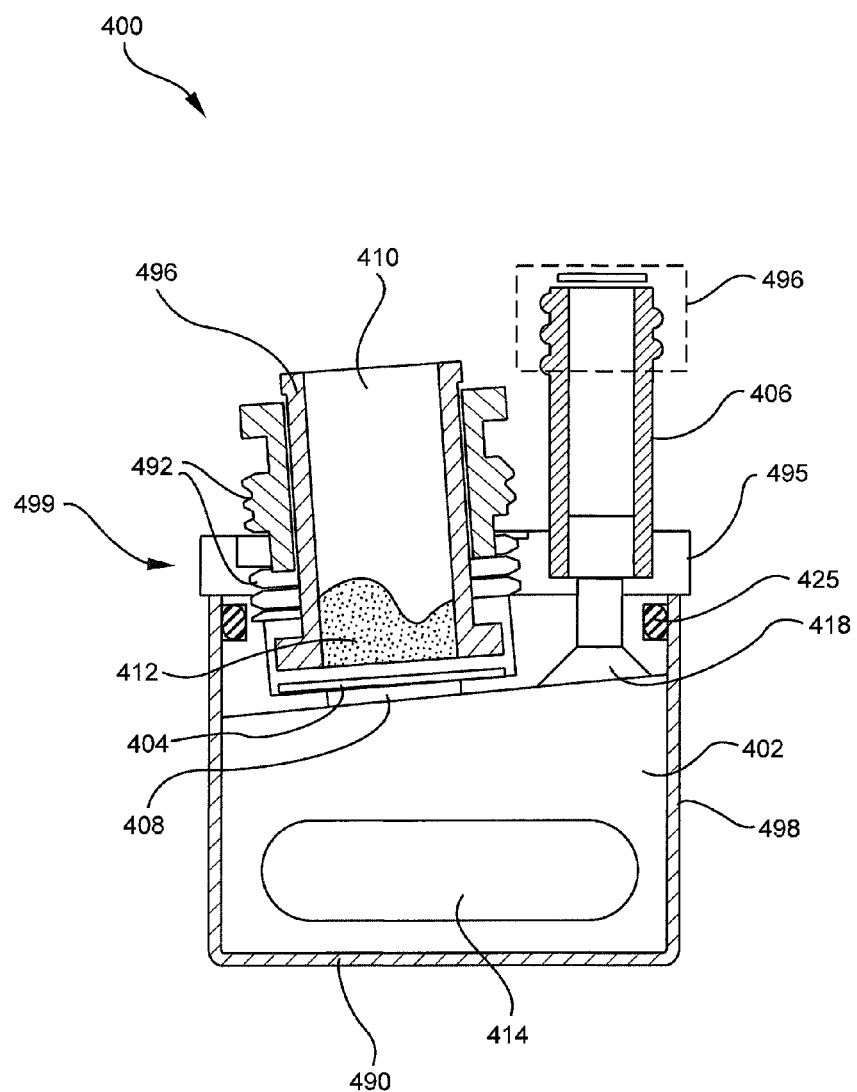
FIG. 8 provides a schematic illustration of an alternative embodiment of a diffusion cell according to the present invention that includes a top section and a bottom section.

FIG. 4, FIG. 5 and FIG. 8 illustrate embodiments of diffusion cells 200, 300, 400 of the present invention that facilitate the automatic migration of bubbles from the underside of the diffusion membrane positioned at the first outlet of the receptor compartment to the bubble trap formed at the second outlet of the receptor compartment. These designs permit bubbles that may be formed near the diffusion membrane to move towards the bubble trap formed by the second outlet without requiring removal of the diffusion cell from a diffusion apparatus or manipulation of the diffusion cell by a human operator (e.g., tilting the diffusion cell to move bubbles into the bubble trap).

As shown in FIG. 4, the first outlet 208 of the receptor compartment 202 can be positioned on a side of the receptor compartment 202 instead of the top. Designing the diffusion cell 200 in this manner effectively rotates the arrangement of the diffusion membrane 204 from a roughly horizontal position to a roughly vertical position. Because the diffusion membrane 204 is positioned vertically on one side of the receptor compartment 202, any bubbles formed within the receptor compartment 202 will tend to rise away from the surface of the diffusion membrane 204 to the top of the receptor compartment 202, where the second outlet 218 and bubble trap are located. In addition, if desired, the top surface of the receptor chamber 202 can form an incline 203 that rises toward the second outlet 218, thereby further increasing the likelihood that any bubbles formed within the receptor compartment 202 will automatically migrate into the bubble trap formed by the second outlet 218, without the need for an operator. The slope 203 should be high enough that air bubbles move towards the opening of sampling port 206. Where the first outlet 208 is positioned at one side of the diffusion cell 200, it is necessary that the association of the diffusion membrane 204, donor compartment 210 and receptor compartment 202 form a seal that prevents leaking of the receptor medium from within the receptor compartment 202. Any suitable mechanism for associating the donor 210 and receptor 202 compartments can be used. The necessary seal at the interface between the diffusion membrane 204, donor compartment 210 and receptor compartment 202 can be formed solely by the mechanism associating the components, or, alternatively, one or more additional sealing members 215 may be included to provide the desired seal. The mechanisms already described for associating the donor compartment and receptor compartment, as well as the additional sealing members described herein are also suitable for use in a diffusion cell designed according to the embodiment illustrated in FIG. 4. Additionally, the receptor compartment may have a stirrer 214.

FIG. 5 and FIG. 8 illustrate diffusion cells 300, 400 according to the present invention wherein both the first 308, 408 and second 318, 418 outlets of the receptor compartment 302, 402 are located at the top of the receptor compartment 302, 402, but the first outlet 308, 408 is designed such that the portion of the top surface of the receptor compartment 302, 402 formed by the bottom surface of the diffusion membrane 304, 404 inclines upward toward the second outlet 318, 418. This tilt or inclination of the top surface of the receptor compartment 302, 402 toward the second outlet 318, 418 of the receptor compartment 302, 402 works to automatically direct any bubbles that form or come to rest on the bottom surface of the diffusion membrane 304, 404 toward the bubble trap formed by the second outlet 318, 418. Additionally, as shown in FIG. 5, the receptor compartment 302, which may contain a stirrer 314, may be disposed within a heating block 319; a top portion of the second outlet 318 may have a cap 315 with a septum, through which may pass a sampling needle 301.

Figure 9:
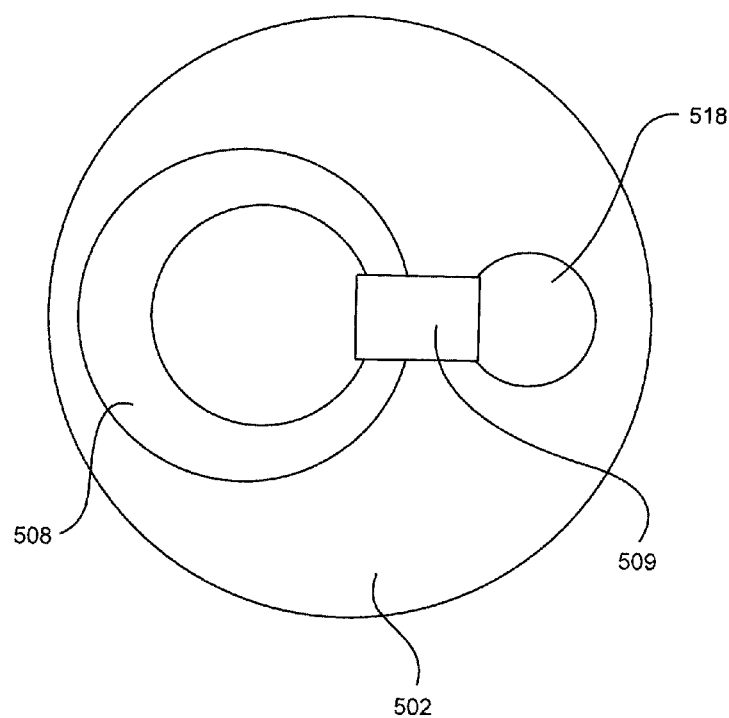
FIG. 9 provides a bottom view of a schematic illustration of a bubble channel that can be formed between the first opening and the second opening in the receptor compartment of a diffusion cell according to the present invention.

In a particularly preferred embodiment, the diffusion cell of the present invention is not only designed with receptor compartment having a top surface that inclines upward toward the second opening, but the diffusion cell also includes a channel connecting the first and second outlets. The channel can simply be a depression formed in the top surface of the receptor compartment that extends between the first and second outlets. An illustration of such a channel is provided in FIG. 9. Typically, the first outlet 508 of the receptor compartment 502 will not be designed such that the bottom surface of the diffusion membrane is flush with the other portions of the top surface of the receptor compartment. Because of this, bubbles may be trapped at the step formed where the bottom surface of the diffusion membrane interfaces with the remainder of the top surface of the receptor compartment. Forming a bubble channel 509 between the first 508 and second 518 outlets reduces any step formed at this interface and thereby further facilitates the automatic migration of bubbles from the bottom surface of the diffusion membrane to the bubble trap formed by the second outlet 518.

The volume of receptor medium contained within a diffusion cell according to the present invention must be considered when designing a diffusion study. Commonly, receptor compartment volumes for diffusion cells range from about 5-30 ml. However, diffusion cells having virtually any desired volume of receptor media can be designed. When it is anticipated that the material to be assayed from the receptor media exhibits a low permeability or flux across the diffusion membrane, relatively small volumes of receptor medium are desirable and may be necessary so that the concentration of the material to be assayed within the receptor medium can be above the limit of detection for the assay method used within a reasonable amount of time. However, when it is anticipated that the material to be assayed from the receptor media exhibits a high permeability or flux across the diffusion membrane, a relatively large volumes of receptor media are desirable and may be necessary to maintain sink conditions in the receptor compartment throughout the diffusion study. Therefore, the volume of the receptor compartment can be varied to provide any particular volume of receptor medium useful for a chosen diffusion study.

Figure 6:
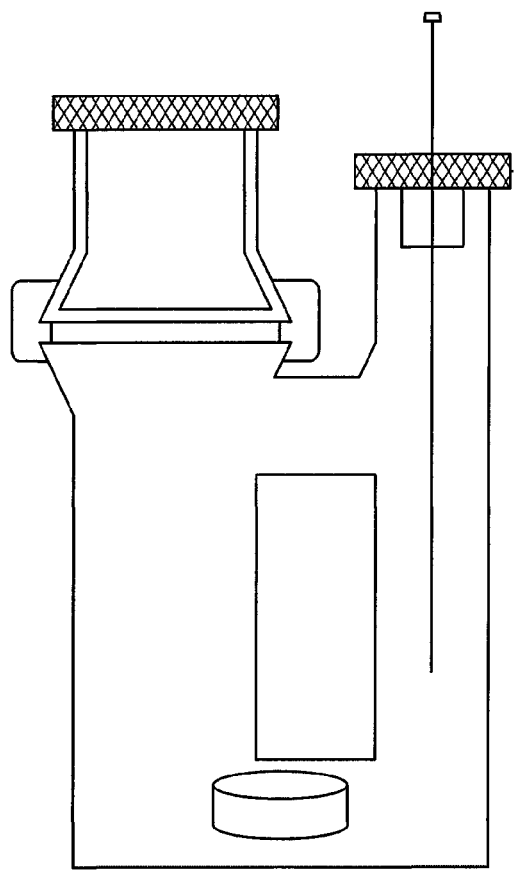
FIG. 6 and FIG. 7 provide schematic illustrations of diffusion cells according to the present invention, wherein the diffusion cells include a top section and a bottom section and the bottom section can be removed and made of different sizes to provide receptor compartments of different volumes.
Figure 7:
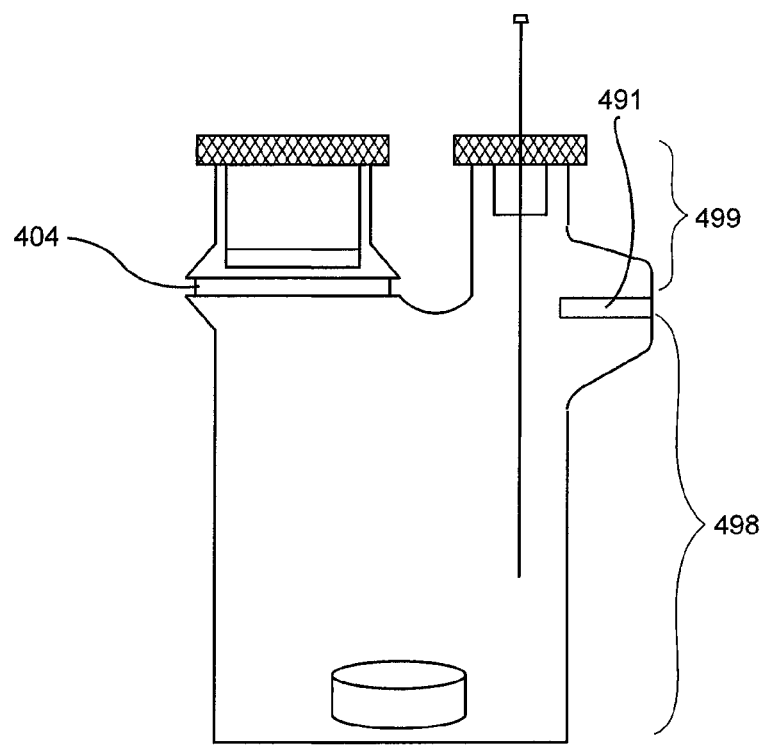

To better facilitate tailoring the volume of the receptor compartment to a chosen diffusion study, the diffusion cell 400 of the present invention can be designed having separable top 499 and bottom 498 sections (shown in FIG. 6-FIG. 8), with a joint 491 between the top 499 and bottom 498 sections. The top section 499 of such an embodiment is formed as a cap and septa 496 or a plug 495, and includes the first outlet 408 of the receptor compartment 402 and integrates an area for association of the donor compartment 410 with the receptor compartment 402, for example by using threads 492. A bottom surface of the top section 499 also forms at least a portion of the top surface of the receptor compartment 402. Preferably, the top section 499 also incorporates the second outlet 418 of the receptor compartment 402 and, as a result, the sample arm 406 and bubble trap of the diffusion cell 400. The bottom section 498 is typically a cup-, well-, or tube-shaped reservoir, which may be made of glass, that is removable from the top section 499 of the diffusion cell. The shape or geometry of the bottom section 498 is preferably designed for efficient stirring of the receptor medium with a stir bar 414. A sealed receptor compartment 402 of a given volume is formed when the top 499 and bottom 498 sections of the diffusion cell 400 are properly associated. By varying the volume of the bottom section 498 of a diffusion cell 400 having separable top 499 and bottom 498 sections, the volume of the receptor compartment 402 can be readily tailored to a meet the needs of a desired diffusion study.

Where the diffusion cell 400 of the present invention is designed with separable top 499 and bottom 498 sections, the two sections 499, 498 of the diffusion cell 400 can be associated using any suitable means. In a preferred embodiment (illustrated in FIG. 8) the top 499 and bottom 498 sections are designed to fit together with a friction or interference fit. In such an embodiment, the top section 499 may include a lip, flange, or other feature that ensures the top section 499 is inserted into the bottom section 498 to a desired depth, providing a receptor compartment 402 having a desired volume. Moreover, to ensure that an adequate seal is formed between the top 499 and bottom 498 sections, the top 499 or bottom 498 section can incorporate one or more sealing members 425, such as one or more O-rings or gaskets. Where the top 499 and bottom 498 sections of a diffusion cell 400 of the present invention are designed to be associated with a friction or interference fit, the force required to associate and dissociate the top 499 and bottom 498 sections should be at least sufficient to maintain the two sections 499, 498 together during a diffusion test and to form an adequate seal where the top 499 and bottom 498 sections interface. Additionally, the diffusion cell 400 may incorporate a sunk area 490 for a complete drain.

It should be understood that top 499 and bottom 498 sections of a diffusion cell 400 of the present invention might also be associated using any other suitable mechanism. For example, the top 499 and bottom 498 sections of a diffusion cell 400 according to the present invention can be associated using a clamp. Alternatively, the top 499 and bottom 498 sections of a diffusion cell 400 of the present invention can be associated using, for example, a threaded connection, a male-female connection or a snap-fit connection. The design of the top 499 and bottom 498 sections of a diffusion cell 400 of the present invention is flexible and can be altered to accommodate the use of virtually any suitable connection mechanism.

The various different components of diffusion cells of the present invention can be fabricated using materials well known in the art. However, in preferred embodiments, at least a portion of the receptor compartment is formed of a glass material. Where the diffusion cell according to the present invention includes a top and bottom section, it is preferable to form the top section of TEFLON® and the bottom section of glass. However, any other materials that are suitable for application in a diffusion cell of the present invention may also be used. For example, instead of TEFLON@, the top section of a diffusion cell of the present invention can be formed of a metal or metal alloy, a polymer material or glass. Moreover, instead of glass, the bottom section of a diffusion cell of the present invention can be formed of a metal or metal alloy or a polymer material. A material is suitable for use in the fabrication of a diffusion cell of the present invention provided it is capable of withstanding exposure to the anticipated test conditions without physical failure and without contaminating the receptor media or retaining undesirable amounts of the material to be assayed.

The diffusion cells of the present invention can be used to conduct a variety of assays used in the art. For example, diffusion cells of the present invention can be used to test various drug dosage forms, including transdermal dosage forms, oral dosage forms, ocular dosage forms such as transdermal or transmucosal patches, tablets, semi-solid dosage forms, gel formulations, pastes, ointments, emulsions, suspension, drops and the like.

Diffusion cells according to the present invention can also be used for mechanistic studies, e.g. transport studies through epithelia that focus on various parameters, such as vehicle effect, ionic strength, markers and the like. The diffusion cells of the present invention can also be used for non-passive diffusion assessments that involve active transport mechanisms, which include iontophoresis, sonophoresis, and the like.

Figure 10:
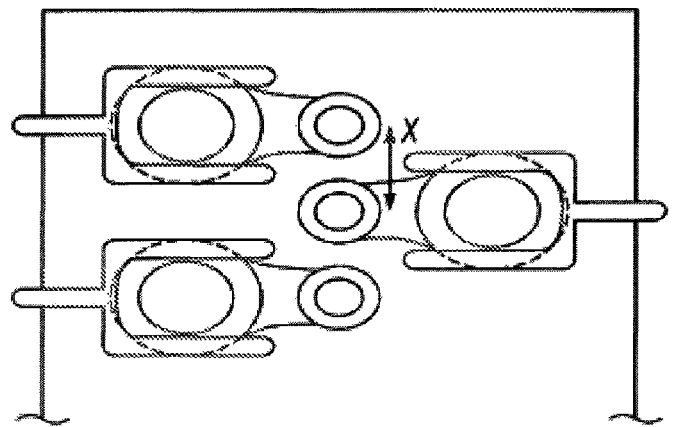
FIG. 10 depicts another example of arranging the static diffusion cells in a mounting apparatus, wherein the sampling ports are lined up in a single row.
Figure 11:
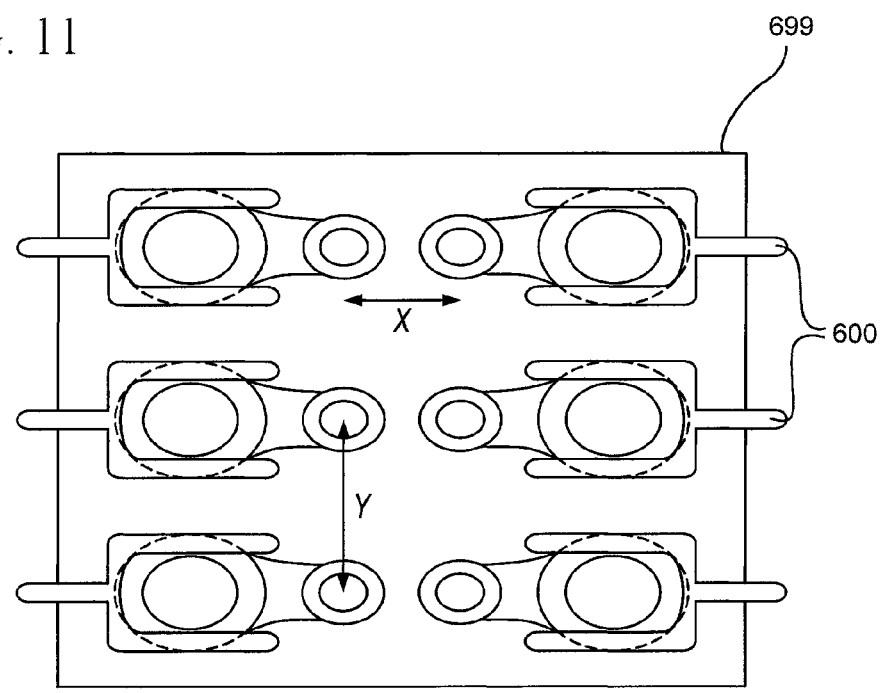
FIG. 11 depicts one example of arranging the static diffusion cells in a mounting apparatus, wherein the sampling ports are lined up in multiple parallel rows.
Figure 12:
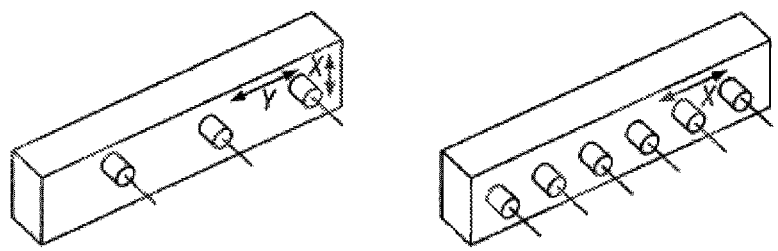
FIG. 12 depicts sampling heads to match a mounting apparatus as illustrated in FIGS. 11 and 10, respectively.

The diffusion cells of the present invention can be used to form a diffusion sampling system. A diffusion sampling system of the present invention includes one or more diffusion cells according to the present invention positioned within a mounting apparatus, such as a mounting block, that allows for stirring of the receptor media in the diffusion cells and serves to maintain the diffusion cells at a desired temperature. Where a mounting block is used, the mounting block is preferably formed of a conductive metal, such as an aluminum alloy or stainless steel, that can be maintained at a substantially uniform temperature throughout the mounting block and allows the use of magnetic stir bars within the receptor compartment. The diffusion cells included in a diffusion sampling system of the present invention are positioned within the mounting apparatus such that sampling ports of each diffusion cell are readily accessible. In preferred embodiments, the diffusion cells include a keying feature that require the diffusion cells to be positioned within the mounting apparatus such that the sample ports are aligned in a configuration that facilitates easy sampling. Once positioned within the mounting apparatus, the diffusion cells can be sampled manually or automatically.

Where automatic sampling of multiple diffusion cells is desired, the diffusion sampling system of the present invention can include, for example, a robot with multidirectional flexibility, such as an XYZ. XYZ robots are often used in high throughput screening applications and are capable of controlled, programmable movements in all directions along the XYZ axes. XYZ robots can also be provided with sampling heads that allow the simultaneous sampling of several cells (generally up to 6 to 12 cells simultaneously). Depending on the positioning of the diffusion cells in the mounting apparatus, different robot sampling heads can be used. Examples of two designs for the blocks and the matching sampling heads are shown in FIGS. 10-12. The static diffusion cells of the present invention are also adapted for manual sampling. FIG. 11 shows a plurality of clamps and cells 600 disposed within a block 699, which may be made of aluminum. The head of an XYZ robot 199 is shown in FIG. 3 interfacing with the present invention cell 100.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention.

We claim:

1. A diffusion cell comprising a receptor compartment and a donor compartment, wherein the receptor compartment is a single-chambered compartment that includes a first outlet and a second outlet, a diffusion membrane and the donor compartment are positioned over the first outlet, and the second outlet forms a bubble trap and a sampling arm, wherein a bottom surface of the diffusion membrane forms at least a portion of the top surface of the receptor compartment and the first outlet of the receptor chamber is formed such that the portion of the top surface of the receptor compartment formed by the bottom surface of the diffusion membrane inclines upward toward the second outlet, and wherein the first outlet and the second outlet are formed at the top surface of the receptor compartment and a bubble channel located in the top surface of the receptor extends between the first and second outlet.

2. The diffusion cell of claim 1, wherein the diffusion cell is formed of a top section and a bottom section and the top and bottom sections are separable.

3. The diffusion cell of claim 2, wherein the top section of the diffusion cell comprises the first outlet of the receptor compartment.

4. The diffusion cell of claim 3, wherein the top section of the diffusion cell comprises the first outlet and the second outlet of the receptor compartment.

5. A diffusion cell comprising a receptor compartment and a donor compartment, wherein the receptor compartment is a single-chambered compartment that includes a first outlet and a second outlet, a diffusion membrane and the donor compartment are positioned over the first outlet, and the second outlet forms a bubble trap and a sampling arm, wherein the receptor compartment includes a top surface, the first outlet and the second outlet are formed in the top surface, and a bubble channel located in the top surface extends between the first and second outlet.

6. The diffusion cell of claim 5, wherein the diffusion cell is formed of a top section and a bottom section and the top and bottom sections are separable.

7. The diffusion cell of claim 6, wherein the top section of the diffusion cell comprises the first outlet of the receptor compartment.

8. The diffusion cell of claim 7, wherein the top section of the diffusion cell comprises the first outlet and the second outlet of the receptor compartment.

9. A diffusion cell comprising
a receptor compartment, which is a single-chambered compartment that includes a first outlet and a second outlet that are located in the top surface of the receptor compartment;
a diffusion membrane and a donor compartment, which are positioned over the first outlet; and
means for removing bubbles located in the top surface extending between the first and the second outlets;
wherein the means for removing bubbles comprises a channel.

10. The diffusion cell of claim 9, wherein the means for removing bubbles further comprises an incline upward toward the second outlet.

* * * * *